United States Patent [19]
Wegner et al.

[11] Patent Number: 6,083,163
[45] Date of Patent: *Jul. 4, 2000

[54] SURGICAL NAVIGATION SYSTEM AND METHOD USING AUDIO FEEDBACK

[75] Inventors: Christian M. Wegner; Daniel B. Karron, both of New York, N.Y.

[73] Assignee: Computer Aided Surgery, Inc., New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 09/009,845

[22] Filed: Jan. 20, 1998

Related U.S. Application Data

[60] Provisional application No. 60/035,945, Jan. 21, 1997.

[51] Int. Cl.⁷ ..................................................... A61B 17/00
[52] U.S. Cl. ........................................... 600/429; 606/130
[58] Field of Search .................................. 600/429, 407, 600/417; 378/205; 606/130

[56] References Cited

U.S. PATENT DOCUMENTS

| | | |
|---|---|---|
| 4,774,515 | 9/1988 | Gehring . |
| 4,905,163 | 2/1990 | Garber et al. . |
| 5,257,998 | 11/1993 | Ota et al. . |
| 5,305,203 | 4/1994 | Raab . |
| 5,402,801 | 4/1995 | Taylor . |
| 5,423,321 | 6/1995 | Fontnot . |
| 5,437,657 | 8/1995 | Epstein ........................................ 606/4 |
| 5,445,166 | 8/1995 | Taylor . |
| 5,513,991 | 5/1996 | Reynolds et al. . |
| 5,546,943 | 8/1996 | Gould . |
| 5,572,999 | 11/1996 | Funda et al. . |
| 5,695,500 | 12/1997 | Taylor et al. ........................... 606/130 |
| 5,711,299 | 1/1998 | Manwaring et al. . |
| 5,792,147 | 8/1998 | Evans et al. ............................ 606/130 |

OTHER PUBLICATIONS

Karron et al., "Extracting 3D Objects from Volume Data Using Digital Morse Theory," Computer Vision, Virtual Reality and Robotics in Medicine, First International Conference, CVRMed '95, Nice, France, Apr. 3–6, 1995, Springer–Verlag, pp. 481–486.

William G. Gardner, "Transaural 3–D audio," M.I.T Media Laboratory Perceptual Computing Sec. Tech. Rpt. No. 342, Jul. 20, 1995, pp. 1–7.

Koch et al., "Simulating Facial Surgery Using Finite Element Models," ACM SIGGRAPH, Annual Conference Series, Aug. 4–9, 1996, pp. 421–428.

Miller Puckett, "Combining Event and Signal Processing in the MAX Graphical Programming Environment," [reprinted from] Computer Music Journal [15(3): 68–77], 1991, pp. 1–16.

(List continued on next page.)

*Primary Examiner*—Marvin M. Lateef
*Assistant Examiner*—Shawna J Shaw
*Attorney, Agent, or Firm*—Pennie & Edmonds LLP

[57] ABSTRACT

A computer based system and method is disclosed for positional guidance in real-time surgical applications using audio feedback. The invention is based on translating the 5 spatial parameters of a surgical instrument or device, such as its position and velocity with respect to a given coordinate system, into a set of audio feedback parameters along the coordinates of a generalized audio space. Error signals which correspond to deviations of the actual instrument trajectory from an optimal trajectory stored in a computer memory are translated into a set of audio signals that indicate to the user whether correction is required. Accordingly, the system and method can be used in a variety of applications that require accurate special positioning. The audio feedback system and method of this invention employ a rich and comparatively unburdened sensory modality in the operating room and can be practiced independent from or along with standard visually-oriented systems and techniques used in medical pre-planning and/or virtual reality devices.

14 Claims, 11 Drawing Sheets

OTHER PUBLICATIONS

Wenzel et al., "A System for Three–Dimensional Acoustic 'Visualization' in a Virtual Environment Workstation," proceedings of Visualization '90 Conference, New York, NY: IEEE Press, 1990, pp. 329–337.

Barrass et al., "Data exploration with sound using a perceptually linearized sound space," CSIRO Div. of Info. Technol., Australia.

Linda World "The Reality of Cybersickness" IEEE Computer Graphics and Applications, New York, IEEE Press, 15(5) p. 95, Sep. 1995.

Stephen Brewster, "Earcons: Providing a Structured Method for Integrating Non–Speech Audio into Human–Computer Interfaces," Ph.D. Thesis, University of York, U.K., 1994.

Lake DSP Pty. Ltd., "General Purposes Analog Audio Converter Modules," Lake Datosheet No. D60113–4, Sydney, Australia: Lake DSP Pty. Ltd., 1996.

Kikinis et al., "Surgical Planning Using Computer–Assisted Three–Dimensional Reconstructions," Computer–Integrated Surgery, Chapter 8, MIT Press, London, England, 1996, pp. 147–154.

Pommert et al., "Three–Dimensional Imaging in Medicine: Methods and Applications," Computer–Integrated Surgery, Chapter 9, MIT Press, London, England, 1996, pp. 154–174.

Rau et al., "Aspects of Ergonomic System Design Applied to Medical Work Systems," Computer–Integrated Surgery, Chapter 12, MIT Press, London, England, 1996, pp. 203–221.

Rosen et al., "Virtual Reality and Surgery," Computer–Integrated Surgery, Chapter 14, MIT Press, London, England, 1996, pp. 231–243.

Bajura et al., "Merging Virtual Objects with the Real World: Seeing Ultrasound Imagery Within the Patient," Computer–Integrated Surgery, Chapter 15, MIT Press, London, England, 1996, pp. 245–254.

Curtis Roads et al., The Computer Music Tutorial, The MIT Press, 1996, pp. 90–107.

Curtis Roads et al., The Computer Music Tutorial, The MIT Press, 1996, pp. 124–130.

Curtis Roads et al., The Computer Music Tutorial, The MIT Press, 1996, pp. 163–184.

Curtis Roads et al., The Computer Music Tutorial, The MIT Press, 1996, pp. 429–432.

Steve Bryson, "Approaches to the successful design and Implementation of VR applications," Virtual Reality Applications, Editors—Earnshaw et al., Part 1, Academic Press Limited, 1995, pp. 3–15.

Richard M. Satava, "Virtual reality for the physician of the 21st century," Virtual Reality Applications, Editors—Earnshaw et al., Part 2, Academic Press Limited, 1995, pp. 19–26.

Benford et al., "Populated information terrains: first steps," Virtual Reality Applications, Editors—Earnshaw et al., Part 3, Academic Press Limited, 1995, pp. 27–39.

Hanqiu Sun, "Hand–guided scene modelling," Virtual Reality Applications, Editors—Earnshaw et al., Part 4, Academic Press Limited, 1995, pp. 41–51.

Slater et al., "Modelling in immersive virtual environments: a case for the science of VR," Virtual Reality Applications, Editors—Earnshaw et al., Part 5, Academic Press Limited, 1995, pp. 53–70.

Fernando et al., "Constrain–based 3D manipulation techniques within virtual environments," Virtual Reality Applications, Editors—Earnshaw et al., Part 6, Academic Press Limited, 1995, pp. 71–89.

Fox et al., "Implementing televirtuality," Virtual Reality Applications, Editors—Earnshaw et al., Part 7, Academic Press Limited, 1995, pp. 91–96.

Alistair D. N. Edwards, Abstracts: "Soundtrack: An Auditory Interface for Blind Users," Human–Computer Interaction, 1989, v.4 n.1 pp. 45–66.

Kennedy et al., "Measurement and Control of Motion Sickness Aftereffects from Immersion in Virtual Reality," Proceedings of Virtual Reality and Medicine: The Cutting Edge, Sep. 3–11, 1994, New York Hilton Hotel, pp. 111–119.

William W. Gaver, Abstract: "The Affordances of Media Spaces for collaboration," Proceedings of ACM CSCW'92 Conference on Computer–Supported Coopertive Work, 1992, pp. 17–24.

William W. Gaver, "Abstract Auditory Icons: Using Sound in Computer Interfaces," Human–Computer Interaction, 1986, v.2 n.2 pp. 167–177.

William W. Gaver, Abstract: "The Sonic Finder: An Interface that Uses Auditory Icons," Human Computer Interaction, 1989, v.4 n.1 pp. 67–94.

SURGICAL NAVIGATION SYSTEM AND METHOD USING AUDIO FEEDBACK

This application claims the benefit of U.S. Provisional Application No. 60/035,945, filed Jan. 21, 1997.

FIELD OF THE INVENTION

This invention is directed to positional guidance systems and methods and more specifically to a surgical navigation system and method using auditory feedback.

BACKGROUND OF THE INVENTION

Modern pre-surgical modeling and planning systems are designed to assist surgeons by allowing them to perform complex tasks such as planing and optimizing tool-paths, manipulatings spaces, excising, harvesting, precisely locating transplantation sites, predicting postoperative results, and others. Such systems are designed to reduce the risks and unknowns in an operating room, and in this regard alone are capable of supplementing the surgeon's own skills and discretion considerably. The focus of much research in this area has been to develop interfaces that can efficiently, effectively, and ergonomically allow surgeons to access volumetric, functional, and trajectory-based navigational data from modeling and planning sessions. The overwhelming thrust of research in the area of surgical modeling and planning understandably has been visually oriented. Recent advances in medical imaging technology (CT, MRI, PET, etc.), coupled with advances in computer-based image processing and modeling capabilities have given physicians an unprecedented ability to visualize anatomical structures in patients, and to use this information in diagnosis and treatment planning. However, visually based systems have proven to have performance problems when running in real-time, which typically renders them unusable except for simulated surgery.

The use of virtual reality in computer-assisted surgical systems is limited in many ways by the present technological level. Thus, for example, limited processing power and real-time rendering places tight constraints on simulations in terms of the sophistication of visually based models. As models become more detailed, more resembling real objects, greater processing power is needed. The head-mounted/heads-up display devices, which are ubiquitous in virtual reality systems are impractical for surgical purposes because they interfere with the surgeon's field of view, and their size and weight produces encumbrance and fatigue. Other factors such as the relatively low scan rates and low resolution further limit the utility of head-mounted display technology for medical use. The devices are discomforting to wear for prolonged periods of time and cause inevitable eyestrain. Furthermore, the latency in image generation and in dynamic head tracking is noticeable in all head-mounted display systems, but is most strikingly apparent in heads-up systems where synthetic imagery is overlaid over the real-world visage.

The implications for computer-assisted surgery based solely on visual processing are disappointing. It is simply unacceptable for the surgeon's speed of motion during an operation to be limited by the demands of the technology. The ultimate goal, after all, is for the technology to remove limitations rather than impose them. Poorly conceived human-machine interface design adversely affects the ability of surgeons to successfully perform procedures. This is unfortunately the case with many virtual reality systems which entangle the surgeon with sensors and instrumentation. Ergonomic design must be a requirement of any system used in the operating room because many parameters already interfere with the intentions of the surgeon and the execution of those intentions by assisting devices. The limitations of the technology should not be further degraded by the interposition of poorly configured interfaces. Technology used in the operating room cannot only be useful in itself, but must be intuitively useable in order to be functionally useful.

Another different but very important limitation of the commercially available technology is that the precision of image-based pre-surgical planning often greatly exceeds the precision of actual surgical execution. In particular, precise surgical execution has been limited to procedures, such as brain biopsies, in which a suitable stereotactic frame is available. The inconvenience and restricted applicability of such a frame or device has led many researchers to explore the use of robotic devices to augment a surgeon's ability to perform geometrically precise tasks planned from computed tomography (CT) or other image data. Clearly the ultimate goal of this research is a partnership between a human and machines (such as computers and robots), which seeks to exploit the capabilities of both, to do a task better than either can do alone. Clearly, computers can be very precise and can process large volumes of data coming from any number of sensory feedback devices. On the other hand, a human surgeon is very dexterous, strong, fast, and is highly trained to exploit a variety of tactile, visual, and other cues. "Judgementally" controlled, the surgeon understands what is going on in the surgery and uses his dexterity, senses, and experience to execute the procedure. However, in order to increase precision within acceptable time limits or with sufficient speed, humans must be willing to rely on machines to provide the precision.

U.S. Patents such as U.S. Pat. Nos. 5,546,943; 5,513,991; 5,445,566; 5,402,801 and 4,905,163 discuss various devices which can be used to assist the surgeon's work. However, none of the prior art discusses in a coherent way the use of another information channel, the human auditory system, for the accurate processing by the surgeons of the huge volume of information generated during an operation.

There exist a number of significant advantages to incorporating audio feedback techniques into applications intended for real-time surgical use. The computational requirements for generating an audio signal are substantially smaller than for graphics, even though the auditory sensory modality is comparatively rich in bandwidth. Because auditory perception is omnidirectional, it is possible to localize sounds emitted from any point in space, even from behind objects, whereas with vision it is only possible to localize objects falling within the viewing frustum. Sound is capable of relating information about the relative distance, azimuth, elevation, and the velocity of a sound source through amplitude, spectral composition and Doppler shifting, respectively. With advanced techniques such as three-dimensional filtering, audio windowing and room acoustic simulation, it is also possible to relate the orientation of objects within a synthetic acoustic space. These observations suggest that the area of information transmission in user interfaces need not be constrained to the size of the monitor or head-mounted display used. Information can emanate from anywhere in space. The fact that audio feedback technology avoids many of the shortcomings of visual systems has already made it an attractive area of exploration.

For example, it has been established that audio feedback can extend the available information transmission bandwidth significantly, in part because humans are capable of processing audio information in parallel. The vertigo caused by rendering latency and scanning, eyestrain, and various etiologies of simulator sickness almost universal in binocular three dimensional systems are not an issue in audio systems.

Accordingly, it is perceived that audio-based real-time intraoperative systems can considerably enhance the utility of modeling and planning technology to surgeons who cannot tolerate the encumbrance of graphical display hardware, and whose visual faculties have preexisting obligations. Presently available systems inadequately exploit these advantages of an independent or supplementary audio feedback system. Therefore, there is a need for a computer system and method for position guidance using audio feedback providing spatial information.

SUMMARY OF THE INVENTION

The present invention concerns a novel computer method and system for positioning guidance based on audio feedback.

In a preferred embodiment, the system of the present invention is based on measurements of the spatial orientation and other positional measurements. In particular, in accordance with the present invention the computer-based system for assisting a surgeon in positioning an article relative to a surgical target path in a patient comprises: means for determining a surgical target path based upon input patient information; sensor means for sensing surgical execution of a surgical target path by the surgeon; and audio feedback means for real-time advising the surgeon based upon a comparison of the surgical target path and the sensed surgical execution.

In a preferred embodiment, the system of the present invention further comprises a memory for storing one or more surgical target paths for the patient. A surgical target path is expressed in a preferred embodiment in terms of two or more spatial coordinates, the values of which are indicative of the desired position and velocity of the article used in the surgical procedure along the surgical target path. In another aspect, the system of the present invention further comprises a means for translating values of the two or more spatial coordinates obtained from the measurement into corresponding values of two or more coordinates of an audio space. In particular, in the system of the present invention each of the two or more coordinates of the audio space may correspond to an audio theme recognizable by the surgeon. Thus, for example, this can be a consonant harmonic structure, such as a major triad, each tone of which corresponds to values along a specific spatial coordinate. In the present invention spacial coordinates are broadly considered as positional (x-y-z) or angular coordinate, acceleration or others.

In another aspect, the system of the present invention further comprises means for automatically selecting different coordinates of the audio space based upon the surgical target path and the sensed surgical execution, so that a surgeon can know how close his hand is moving to a desired path simply by listening to the audio feedback. Notably, unlike visual systems, which require full attention from the human for certain periods of time, an operating surgeon can correct his movements virtually without a distraction. Naturally, the system of the present invention can further be supplemented by corresponding visual feedback means for advising the surgeon.

In accordance with another embodiment of the present invention, a computer based positioning method is disclosed for assisting a surgeon in positioning an article relative to a surgical target path in a patient, comprising the steps of: determining a surgical target path based upon input patient information; sensing surgical execution of a surgical target path by the surgeon; and providing audio feedback for real-time advising the surgeon based upon a comparison of the surgical target path with the sensed surgical execution.

BRIEF DESCRIPTION OF THE DRAWINGS

The foregoing aspects and other features of the invention are explained in the following description, taken in connection with the accompanying drawings, wherein.

DETAILED DESCRIPTION

Figure 1:
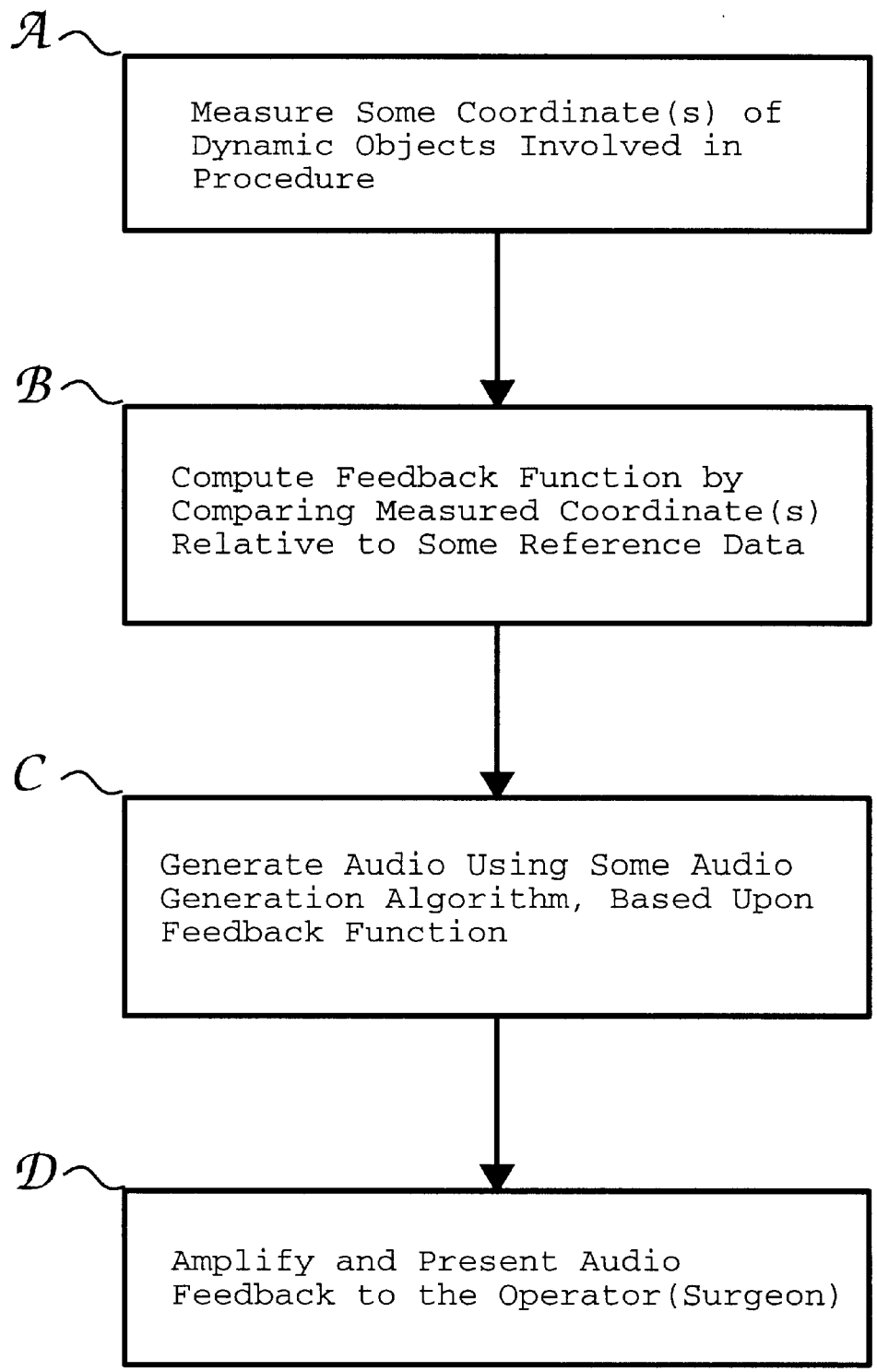
FIG. 1 shows a block diagram of the system hardware built in accordance with a specific experimental embodiment of the present invention.

The foregoing aspects and other features of the invention are explained in the following description, taken in connection with the accompanying drawings. There are a number of established methodologies for using integrated sound in computer applications and embedded systems. Sound has commonly been employed as a redundancy measure in computer games and virtual environment simulations by reinforcing other sensory elements in the simulation, such as graphical or haptic. Symbolic sound structures have also been used in the manner of icons in musical user interfaces (MUI's) developed for the blind (see Edwards, A.D.N., 'Soundtrack: An Auditory Interface for Blind Users,' Human Computer Interaction, 4(1), 1989). With this approach musical sound, sound effects and sampled speech form auditory icons [14], which may be manipulated within an audio desktop space. See Wenzel, E. M.; Fisher, S.;

Stone, P. K., Foster, S. H. 'A System for Three-Dimensional Acoustic "Visualization" in a Virtual Environment Workstation.' Proceedings of Visualization '90 Conference. New York, N.Y.: IEEE Press. 1990.

Related approaches have included warning systems for civil aircraft and simple audio feedback systems for medical equipment. See Patterson, R. D., 'Guidelines for Auditory Warning Systems on Civil Aircraft.' (Report No. 82017). London, U. K.: Civil Aviation Authority, 1982; and Patterson, R. D., 'Alarm Sounds for Medical Equipment in Intensive Care Areas and Operating Theaters,' Report No. AC598, Institute for Sound and Vibration Research, University of Southampton, U.K.

Interface design for providing positional or orientational guidance using audio feedback is still in an experimental stage. Still, it includes applications as diverse as an experimental three-dimensional auditory 'visualization' system, the NASA Ames Virtual Interactive Environment Workstation (VIEW) system, and targeting for tactical aircraft. See Mulder, J. D.; Dooijes, E. H. 'Spatial Audio in Graphical Applications.' Visualization in Scientific Computing. New York: Springer-Verlag; 1995. Wenzel, E. M.; Fisher, S.; Stone, 35 P. K., Foster, S. H. 'A System for Three-Dimensional Acoustic "Visualization" in a Virtual Environment Workstation.' Proceedings of Visualization '90 Conference. New York, NY: IEEE Press. 1990; and U.S. Pat. No. 4,774,515.

These position guidance systems generally employ simple algorithms which convert a few dimensions of position data into corresponding acoustical dimensions. Additionally, three-dimensional audio processing filters are frequently used to reinforce the sense of spatial position. E. M. Wenzel describes using frequency beat interference between two sound sources as a means for providing feedback for properly positioning a circuit board in a NASA astronaut training simulations. This approach could easily have cross applications to surgical placement tasks.

The present invention is based, in part, on the understanding that the interface design methodology employed by musical instruments may serve as a model for systems which aim to provide positional guidance by means of audio feedback. Musicians control the pitch and various expressive aspects of their performance by positioning their hands relative to their instruments. In the case of variable pitch instruments—instruments without discretized pitches—such as fretless stringed instruments, the slide trombone, or the therein, the manual control position must be extremely precise for the note to sound correctly. A variable spatial precision measurable in the extreme to fractions of a millimeter is a requirement for competent performance upon an instrument such as the violin.

Instrument interfaces generally present a single axis of control with respect to pitch, for instance the musician's finger sliding up and down a string. There are numerous other axes of control specific to each instrument used for controlling aspects of the performance, such as amplitude and spectral characteristics. In playing the classic electronic musical instrument known as the therein, invented in 1928 by Leon Therein, the musician controls both pitch and amplitude by moving his/her hands in the air, relative to two antennae.

Our invention is based on an conceptual inversion of the standard paradigm of performance upon a musical instrument, such as the therein—using position to control sound—so that now sound can be used to provide feedback as to position in surgical placement tasks.

Virtual Audio and Medicine

One of the specific advantages of incorporating audio feedback into medical applications concerns the requirement for the surgeon to maintain an extraordinary degree of focus on the task at hand. In this context, information supplied by the assisting system must be intuitive and information-rich without distracting the surgeon from the procedure. Integrated spatial audio systems function well in high-stress applications. For example, in aircraft cockpits employing integrated audio displays, the focus of attention between virtual sound sources and other information sources can be switched at will; whereas vision requires physical movement. See Bly S. 'Presenting Information In Sound,' Proceedings of the CHI '82 Conference on Human Factors in Computing Systems. New York: ACM.

This has a clear cross-application to the demands of the surgeon. Conditions in the operating room are analogous in many ways to the aircraft cockpit, particularly in the audio dimension, where equipment sounds emanate from many locations.

The System

A preferred system architecture for the present invention can be generally described as two subsystems or groups; a presurgical modeling and planning system and a corresponding method, and the audio feedback surgical system substantially as described herein. The presurgical system and method generally uses models of patient information to assist the surgeon in planning precise surgical procedures. Any suitable type of presurgical system and method could be used. For example, one can use the system described in U.S. Pat. No. 5,445,166, which is incorporated herein for all purposes.

Thus, for example, in one type of presurgical procedure, described below for informational purposes only, the principal components of this presurgical procedure include a medical image database and display system, an anatomical model builder, an anatomical feature extractor, a surgical simulator, an anatomical data base, and a surgical plan optimizer. These components are used to produce a surgical plan. The medical image database and display system can be used, for example, to support archival, retrieval, low-level processing, and display of CT, MRI, and other images. The anatomical model builder transforms recorded images into three-dimensional solid models of the patient's anatomy. In the second step (model reconstruction), a boundary representation of each connected set of tissue is constructed by an appropriate algorithm. In the third step, coplanar faces are merged to reduce the size of the model somewhat. Implementation of this process can be semi-automatic, in which a technician "seeds" the search by identifying points on or near ridge curves, and the computer then locates and follows the ridge curves. A more automatic procedure may, of course, be used.

The surgical system and method preferably includes a surgeon interface system and passive manipulation aids. The surgeon interface uses a variety of modalities such as graphics, synthesized voice, tonal cues, programmable impedance of manipulator joints, etc., to provide online, realtime "advice" to the surgeon, based on the sensed relationship between the surgical plan and surgical execution. A quite sophisticated, "intelligent" system can be used that uses its model of the surgical plan to automatically customize displays, select appropriate sensor tracking modes, and help interpret inputs from the surgeon. In this system, a helmet-mounted sterographic display could be used to project the surgical advice directly onto the surgeon's visual field, and the surgeon could use voice input to tell the system what the surgeon wants. In a basic system, very simple real-time graphics and auditory cues can be provided for alignment.

The second component of the system in accordance with the present invention is the audio feedback system. The challenge faced in developing a feasible methodology for designing a position feedback system is to formulate an approach for transforming instrument and anatomical model data, of the type discussed above, into a comprehensible audio feedback signal that would be optimally intuitive, information-rich, ergonomic and economical in terms of the learning curve for users.

Some notable obstacles to developing such a feasible methodology exist. Such are, for example, numerous psychoacoustic phenomena—especially the nonlinearity of human hearing—which conspires to perplex even simple applications, and the problem of determining frames of reference for users. Basically, the problem of determining reference frames can be stated as the decision as to the appropriate mapping of axes of virtual space to the user's coordinate system, and to the real world.

The exploitation of mapping reference frames in interface design is more common than one might imagine: consider how computer users have little trouble overcoming the positional translations which occur between a horizontally manipulated mouse, and a vertically projected cursor. The interface has a surprising intuitiveness despite the fact that the y and z axes may be reversed x offset +/−n depending upon the placement of the mouse (and the handedness of the user) -possibly even the magnitude of movement scaled. The correspondence is simple and consistent; the expected outcome of shifting the mouse in x, z does not diverge too significantly from the actual movement of the cursor.

Mapping geometry into sound is a larger strain upon the cognitive faculties of the user than the simple transformations and scaling of the computer mouse to monitor/cursor interface. Instead of translating one or more dimensions into another within a homomodal space, the synesthetic approach involves transmodal mappings, in the case of the present invention the mapping of geometry into a corresponding aural space. In order for the system to be at all useful, the cardinal task is to determine which dimensions of the initial modality are to be mapped to the resulting modality. For systems requiring as high a degree of confidence in performance as computer-surgical systems, the chosen configuration must result in the greatest possible intuitiveness of the interface. Perceptual issues here become keenly important if the transformation/mapping is desired to be as lossless as possible because, of course, the visual and auditory physiognomic and cognitive manifolds have differing, even incomparable, perceptual resolutions (minimum perceptual differences), perceptual ranges, nonlinearities of response (e.g. frequency/intensity response in hearing), etc.

Musical Structural Functions

In addition to the basic audio primitives such as waveform, frequency, gain, phase, etc., musical informatics presents a large number of combinatorial structural functions which are open for consideration in developing a surgical sonification system. These allow significant flexibility in developing sonification methods. Some of these function classes are:

Harmonization: procedures for specifying simultaneous occurrences of n>1 frequency sources (i.e., vertical procedures).

Counterpoint: procedures for specifying intervallic layering of simultaneously occurring melodic lines (i.e., horizontal procedures).

Rhythm: repetition patterns of temporal-proportional spacing of audio events.

Modality: use of frequency-class sets (ordered pitch sets, consonance, dissonance).

Orchestration: juxtaposition of frequency and spectral relation structures.

Large scale structure: global instances of repeated or related patterns in any musical dimension.

Development processes: strategic occurrence of the following transformations of large scale structures in any musical dimension(s): modulation, liquidation, augmentation, diminution, inversion, retrogression, etc.

Algorithmic procedures employing some of these high level functions could impart a greater listenability and coherence to the feedback system overall, as opposed to a purely low-level approach where the feedback semiotic does not extend beyond the variation of physical acoustical parameters, to which the ear might desensitized. They will also allow the communication of multiple high-level coordinates in a artificial formal language to the surgeon.

Experimental Position Feedback System (System 1)

An experimental audio feedback system was assembled in accordance with the principles of the present invention using inexpensive commercially available hardware. In a specific embodiment, the hardware platform was chosen more with an interest in rapidly assembling a working prototype which could be used to demonstrate the design concept than with the intent of assembling a prototype with a high quality of performance. The prototype is based on the existence of a specialized real-time audio/synthesis programming kernel suited to perform the task on a low level (MAX) for MacOS and uses a high-end Macintosh clone (FIG. 2, Group B, Block 5) and programming the applications in MAX and C.

Hardware Description for System 1

Figure 2:
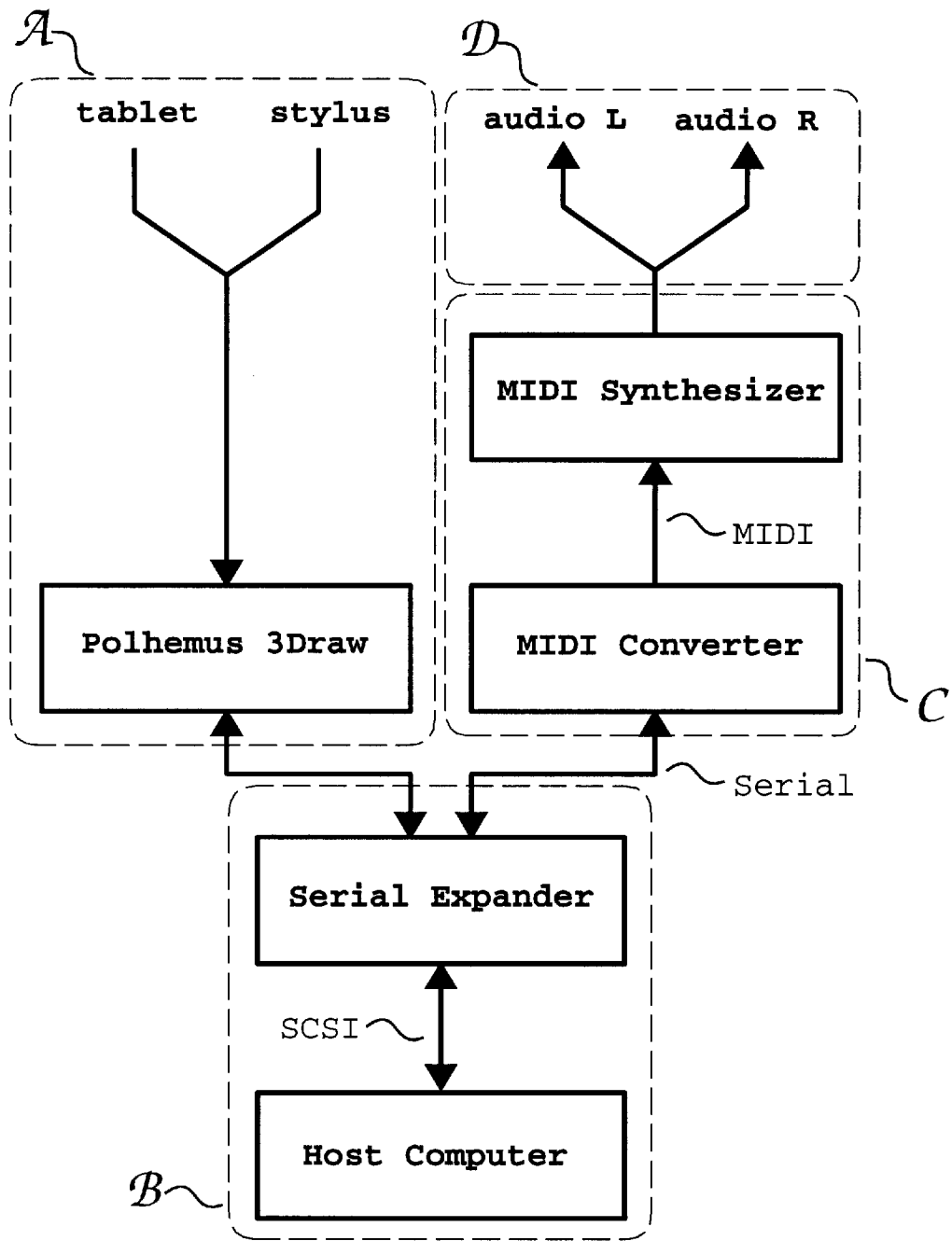
FIG. 2 shows a block diagram of the system hardware built in accordance with a specific embodiment of the present invention.

In a preferred embodiment, the system host was a PowerPC 604e (225 Mhz) workstation running MacOS 7.5.5 (FIG. 2, Group B, Block 5). The sonification subsystem consisted of a KORG 05R/W synthesis module (FIG. 2, Group C, Block 7) with a 31.25 Kbit serial connection (FIG. 2, Group C, Block 6) to the host computer. Stereo audio output is fed to a pair of headphones or an amplifier and speakers (FIG. 2, Group D, Block 8). The position tracking subsystem consists of a Polhemus 3Draw device (FIG. 2, Group A, Blocks 1–3) connected to the host via a CSI SCSI serial interface (FIG. 2, Group B, Block 4) running at 115,200 baud. The system of the present invention in the specific embodiment discussed above is further illustrated in FIG. 2.

Sound Synthesis and the MIDI Standard

The audio feedback system of the present invention was implemented in a specific embodiment using commercially available synthesis modules adhering to the MIDI standard. Naturally, pure software, or a DSP/software hybrid approach to synthesis can also be used in alternative embodiments. The audio devices of the selected system have much to offer in terms of reliability, usability, simplicity. The speed of operation and quality of sound is very high in comparison to software-based systems because the hardware is dedicated solely to wavetable playback. Sound programs can be designed, but they are more or less static during execution. Although the sounds can achieve a very sensuous quality with layering of many subprograms, the sounds have limited application because all but a few parameters cannot be controlled in real-time. This relatively restricted functionality is due to the limitations of the Musical Instrument Digital Interface (MIDI) standard. The MIDI standard is a hardware specification and protocol for connecting synthesis modules with computers. MIDI was designed for real-time control of audio/synthesis devices. Transmissions under this specification operate at a rate of 31.25 Kbits/sec, asynchronous. The communications signals, which consist of a start bit, an 8-bit data byte and a stop bit, contain control data, like switching a sound on and then off, changing the output pitch of an oscillator, or changing a preset timbre program, instead of transmitting actual sound waveforms. The controlling computer produces a stream of amplitude and pitch envelope information. See Roads, C., The Computer Music Tutorial, Cambridge: MIT Press, 1996. The MIDI specification carries many limitations with it in terms of the range of control. All control functions are limited to 128 states. For instance, one cannot choose an arbitrary frequency of, say, 440.09 Hz. The pitch control instruction is an integer within the range 0–127. In fact, pitch instructions do not actually represent absolute pitches, but simply instruct the synthesis module to use the preset frequency in storage that corresponds to that index, whatever that might be.

Figure 6:
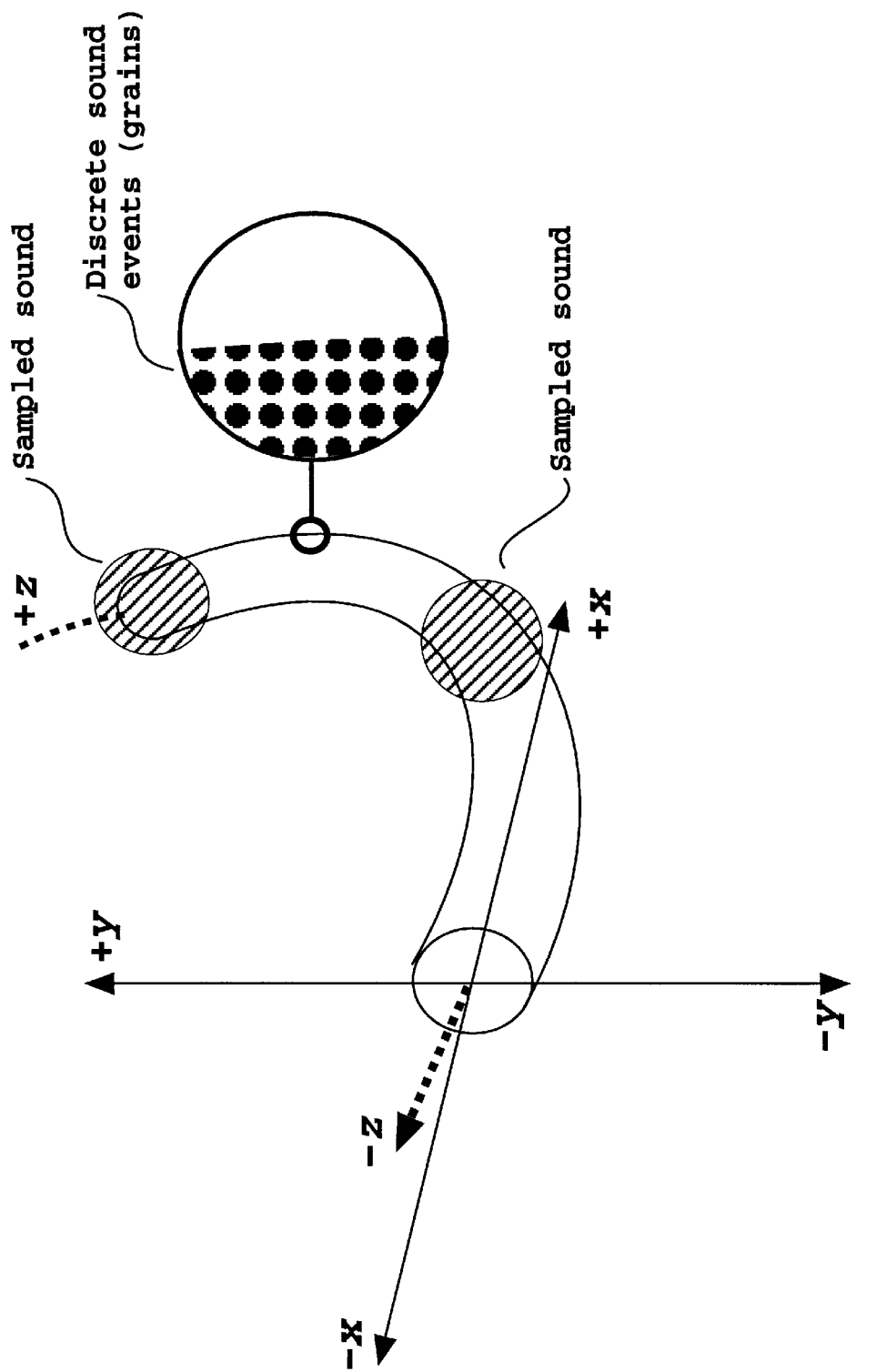
FIG. 6 shows a multidimensional error function employing three-dimensional sound filtering of the signal used in a preferred embodiment of the present invention to advise the surgeon of deviations from a target surgical path.

Implementation of Position Sonification: FIG. 6

As noted above, the sonification approach used in the system of the present invention was to some extent constrained by the MIDI specification, which requires the use of feedback as a discrete rather than a continuous error function. The KORG synthesis module (FIG. 2, Group C, Block 7) allows a maximum of sixteen independent voices, often considerably fewer, depending upon the complexity of the sound program. In the following example, design applications for position feedback are only discussed with reference to a single rigid body and neglect orientation and other dynamics (such as velocity and torsion). The application employed a simple GUI for designing trajectories in three dimensional space, allowing a three dimensional resolution of 0.001 of an inch (which is roughly equivalent to the Polhemus 3Draw device's (FIG. 2, Group A, Blocks 1–3) positional resolution of 0.005 of an inch) . Two sound generating subsystems were employed as a part of the overall system: MIDI synthesis via an external synthesis module, and AIFF sample playback, using the Mac OS sound manager (FIG. 2, Group B, Block 5). The MIDI subsystem (FIG. 2, Group C, Blocks 6–7) is used to generate a discrete error function for error in the y, z planes, and the AIFF subsystem to allow the user to tag specific locations on the target path along the x axis. A GUI allowed the user to specify the radii of the MIDI error envelopes, sound programs, pitch, and amplitude. A number of AIFF samples of recorded speech and sound effects were provided. The user could set the sample volume, playback triggering radius from the target path center in the y, z plane, and the point along the target path in the x axis where playback would occur. As the instrument nears its target path, the targeting feedback pitch for x approaches the lowest pitch of the consonant triad, thus, when the target is reached, harmonic stability is attained.

Preferred Embodiment Position Sonification System (System 2)

Hardware Description:

The Huron Digital Audio Convolution Workstation (FIG. 3, Groups B, C, Blocks 4–9) is a rack-mounting industrial PC (FIG. 3, Group B, Blocks 4–6) fitted with a combination ISA bus and Huron bus backplane allowing standard bus boards as well as Huron DSP boards (FIG. 3, Group C, Block 8) and I/O boards (FIG. 3, Group C, Block 9) to be installed.

Figure 3:
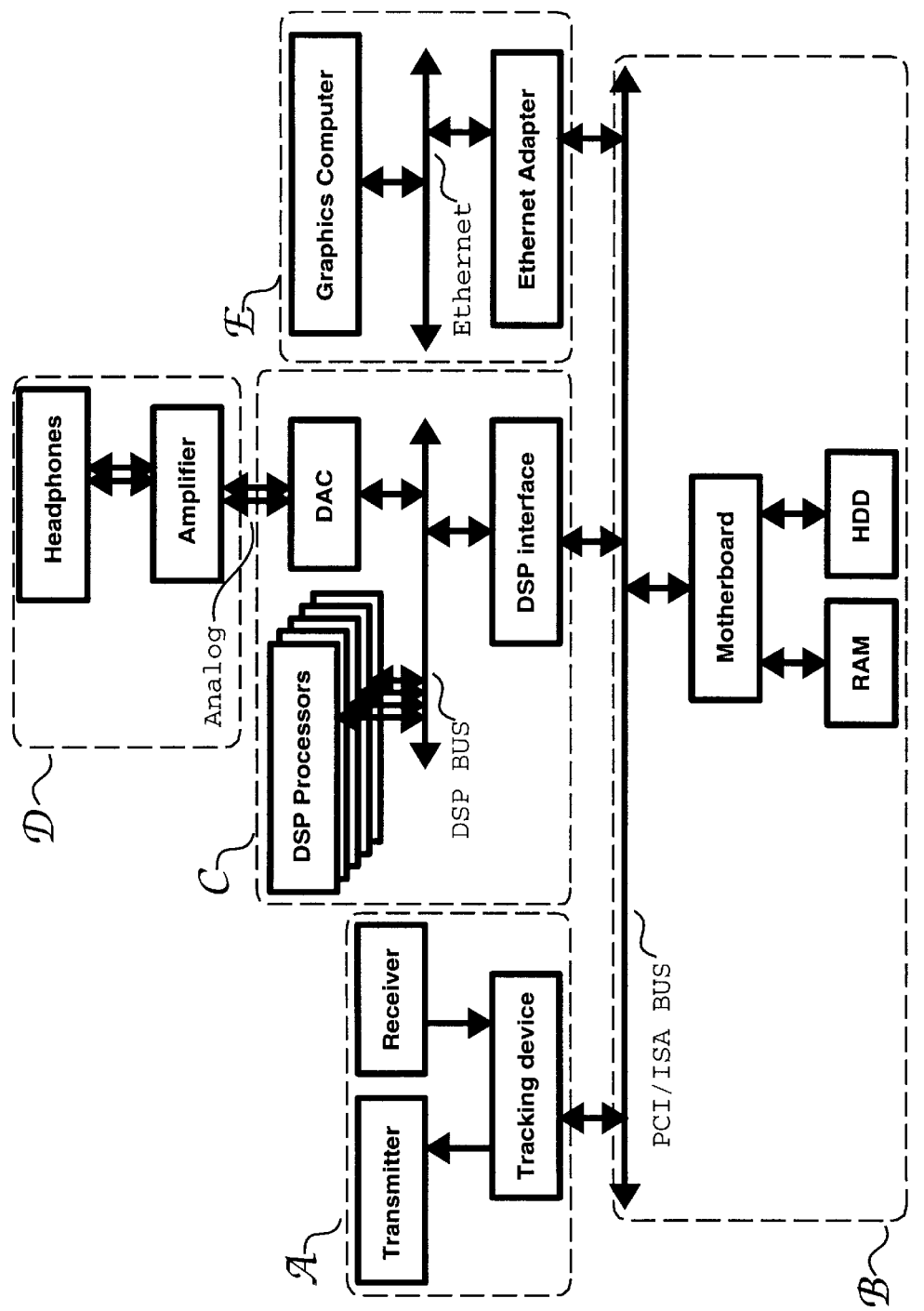
FIG. 3 is a conceptual diagram depicting the relationship between the software programs comprising the various subsystems and memory banks the system in accordance with the present invention.
Figure 4:
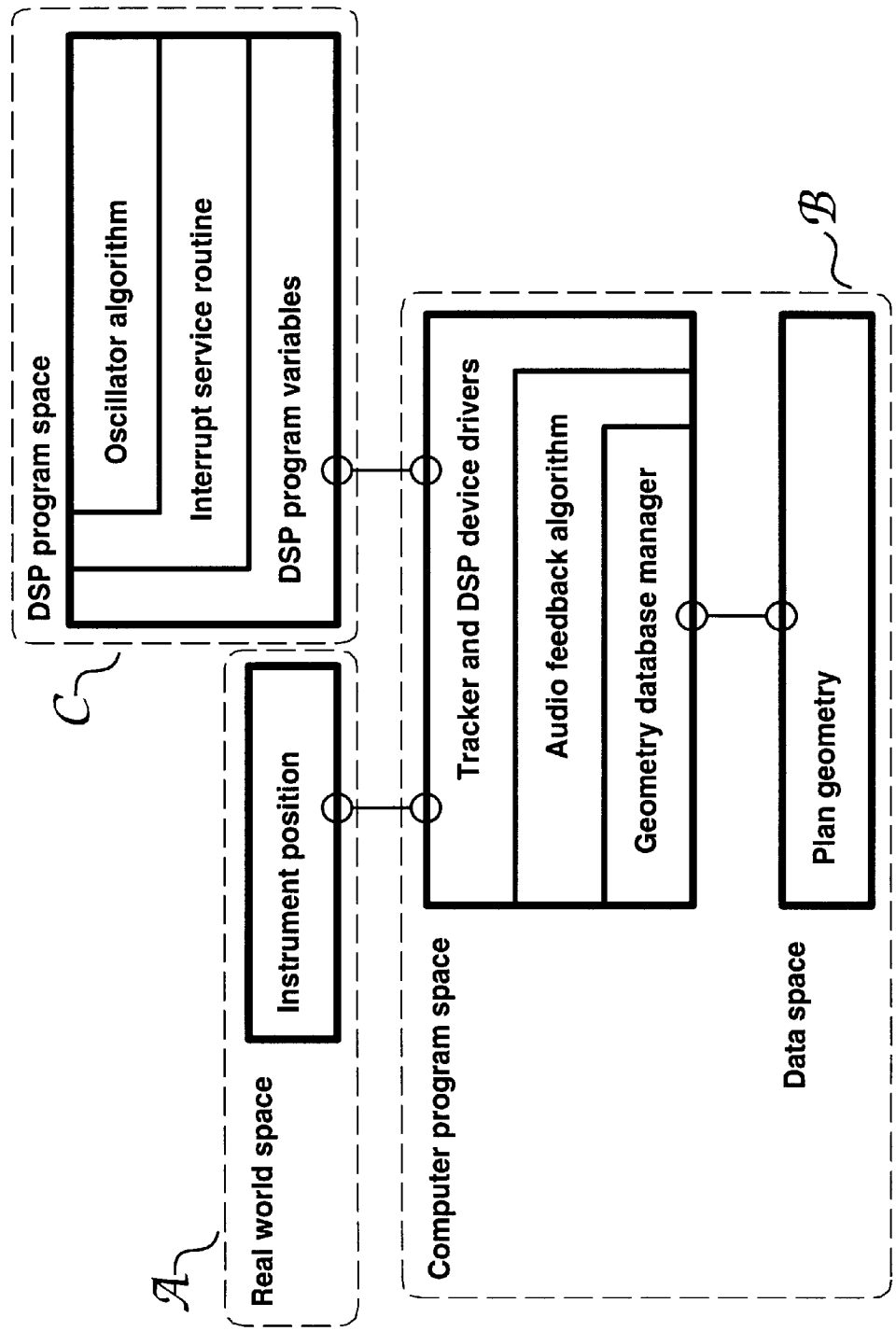
FIG. 4 is a functional block diagram depicting the overall functioning and flow of data of the system used in a preferred embodiment of the present invention.
Figure 5:
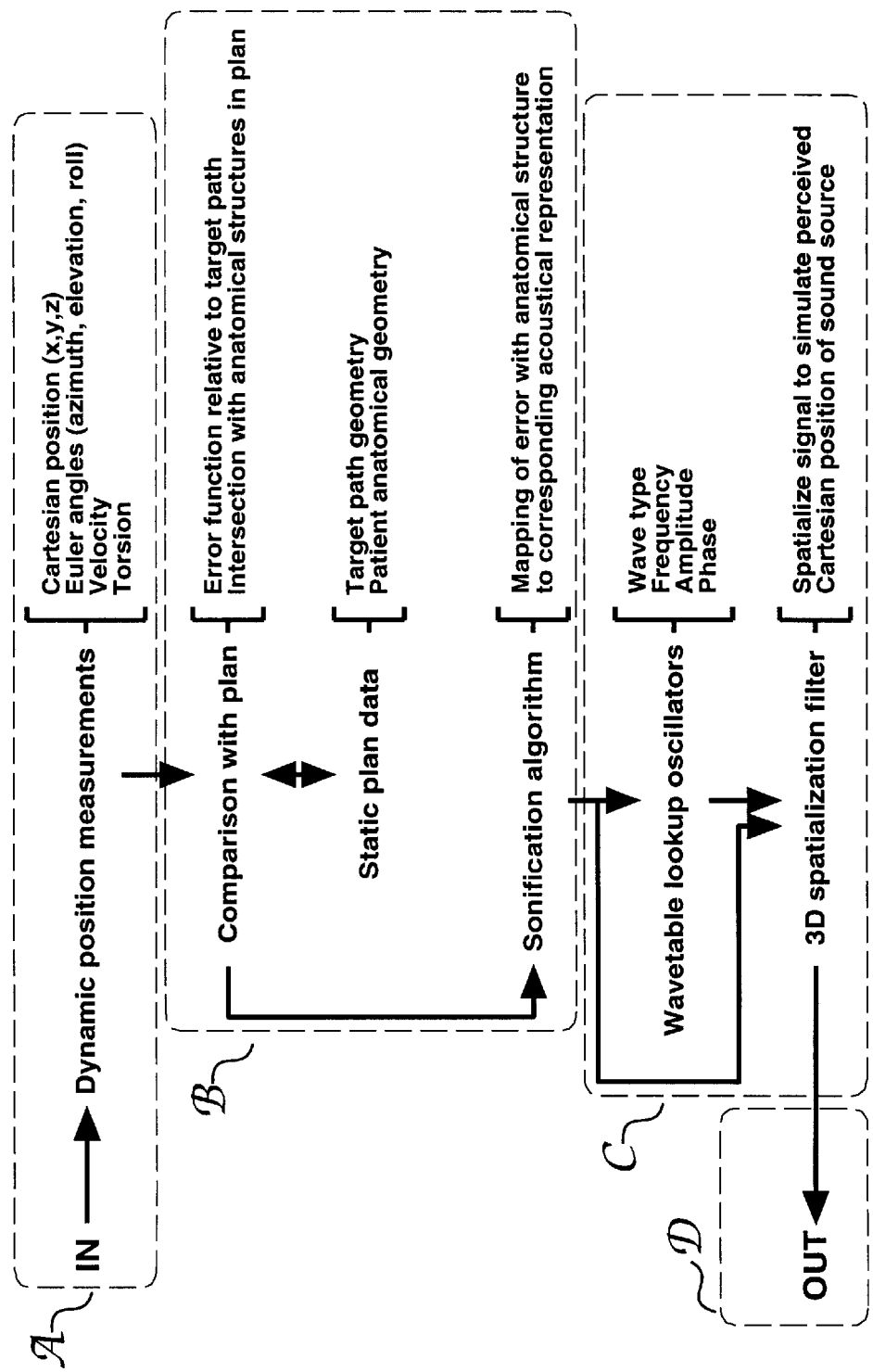
FIG. 5 shows a multidimensional error function used in a preferred embodiment of the present invention to advise the surgeon of deviations from a target surgical path.

DSP Boards/Processors (FIG. 3, Group C, Block 8)

The Huron DSP board is a high performance, multiple-processor audio DSP engine. The Huron DSP board interfaces with the Huron bus, which is a 256-channel 24-bit Time Division Multiplexed (TDM) audio bus, that provides low-latency communication to I/O boards and other Huron DSP boards in a Huron Digital Audio Convolution workstation. Up to 20 boards maybe installed in the Huron digital audio convolution workstation providing significant audio signal processing capacity for audio rendering and other three-dimensional audio processing appropriate for the project. The Huron architecture features 12 Mbytes of fast page-mode (zero wait state without page) Dynamic Random Access Memory (DRAM) and 1.5 Mbytes of Static RAM (SRAM).

Each Huron DSP board supplies four processors of the Motorola D5P56002 chipset (40 MHz clock). Each processor may read or write to any of the 256 TDM channels which form the external Huron bus but may also read or write to an additional 512 TDM channels available on the DSP Board. This allows up to 768 TDM channels for inter-processor communications where 256 channels allow communication to processors or audio interfaces located on other boards and 512 channels are for communication between processors on the board. The Huron DSP board supports up to 4 channels of Lake Convolution (Lake's proprietary low-latency long convolution algorithm), allowing the implementation of FIR filters of up to 278,244 taps in length without latency.

I/O Board (FIG. 3, Group C, Block 9)

The Huron I/O carrier board permits both analog and digital audio signals to interface with the Huron system. The Huron I/O system is a flexible and modular design where compact, 2-channel interface modules are installed on the Huron I/O carrier board as required for the variable needs of our application. Up to eight I/O modules may be installed allowing 16 total I/O channels. Digital audio output is provided via a 2-channel digital output module. Digital audio output is at the system sampling rate (48 kHz).

Figure 8:
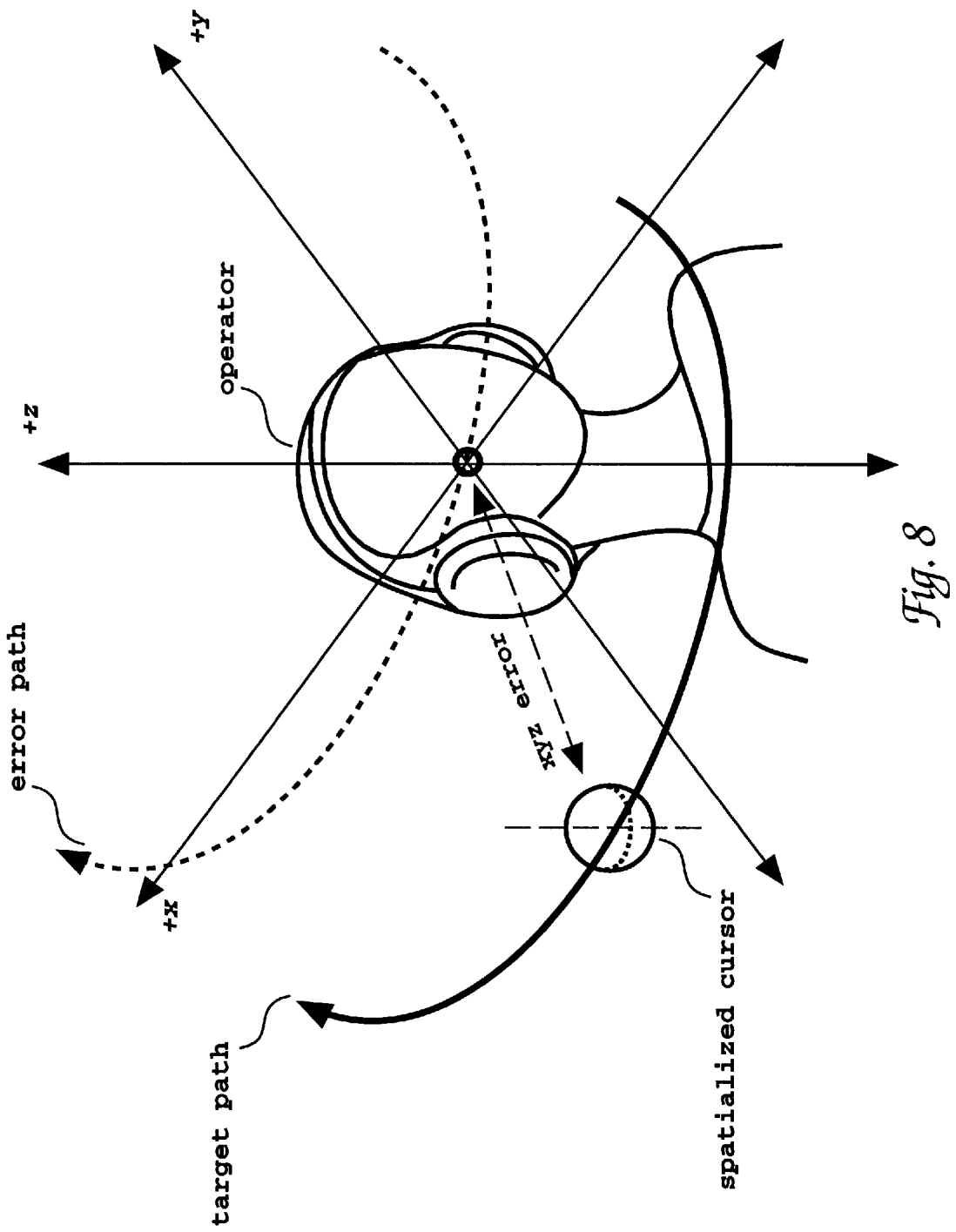
FIG. 8 shows a method for rendering into sound the geometry, density, histological type, or any other dimensions of the patient's anatomy or physiology to be used in a preferred embodiment of the present invention to advise the surgeon of deviations from a target surgical path.

3-D Audio Filtering Tools (Implementation FIG. 8)

Our implementation employs Lake's sound field simulation and auralization software. The AniScape software system comprise the three-dimensional spatialization component of the implementation of the invention, in applications for the simulation of acoustic spaces for playback over headphones or loudspeakers.

AniScape offers flexibility in the design of interactive virtual acoustic environments with moving sound sources, and control in real-time. Simulations using this system provide a high degree of realism through the use of proven acoustic modeling methods, in conjunction with Lake DSP's long, low-latency convolution technology (Lake Convolution). AniScape gives total control of the locations of multiple sound sources and listeners within a virtual acoustic space.

Sound sources are encoded into a general three-dimensional audio format by grouping their position and orientation, the position and orientation of the listener and the acoustic properties of the synthetic space they inhabit. This generalized format is composed of just four standard audio signals and may be decoded to headphones using a binaural decoder. The simulated acoustic space used is implemented in real-time using a highly detailed room response.

Synthesis Approach

Following is a discussion of a number of synthesis techniques which are applicable to the problem of developing DSP-based audio synthesis algorithms, but not inclusive of all possible or preferred techniques. In this context, this discussion is only intended to suggest certain sound synthesis methods with respect to the described example feedback algorithms.

Wave-table Lookup: Fundamentals of Synthesis

The basis of at least one class of synthesis approaches is a wave-table lookup-based oscillator implementation. In our example hardware configuration this is implemented by using banks of sine-wave oscillators on the Motorola DSP56002 chipset. With the availability of precision digital signal processors, such as the Motorola DSP56K family, stable and low distortion sine waves of arbitrary frequency can be produced using wave table look-up with interpolation to reduce distortion. The wave-table is scanned by means of an index that is incremented at each sample period. This table-lookup approach is industry-standard, and serves as the basis for granular synthesis as well as additive synthesis.

Figure 10:
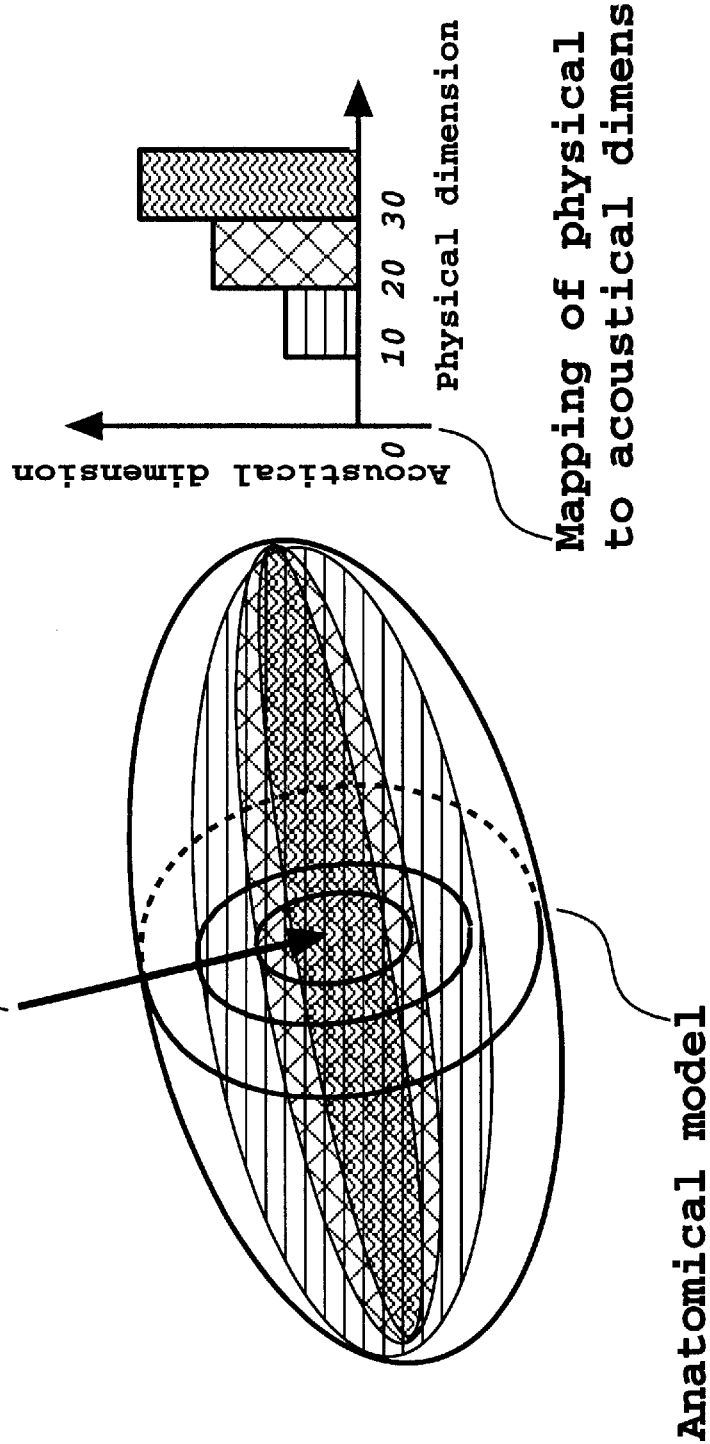
FIGS. 10–11 provide an illustration of the granular synthesis-based anatomical sonification function generated in a specific embodiment.
Figure 11:
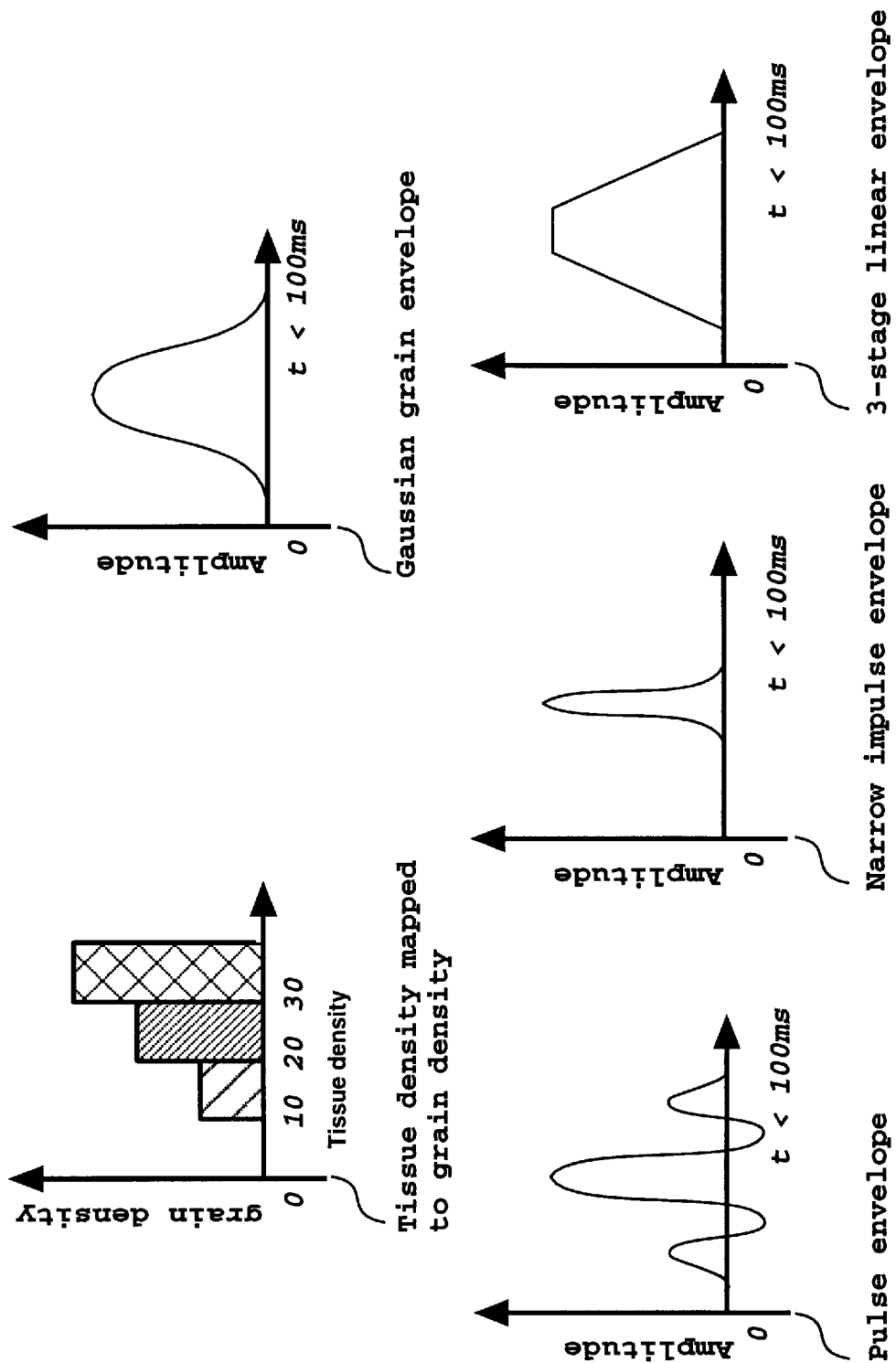

Granular Synthesis: Clouds of Sound (FIGS. 10 to 11)

Granular synthesis has a useful application in sonification because it permits the sonification of gradients using variable density clouds of sound particles. In a granular system, sound can be viewed in terms of both wavelike properties and particulate properties just as light energy (photons). Granular synthesis aggregates acoustic events from thousands of sound grains. These sound grains typically last from 1 to 100 ms. This range of duratmin approaches the minimum perceivable time for event duration, amplitude, and frequency discrimination. A particular anatomical object three-dimensional volume may be propagated with a particular type and density of sound grain. Penetration of this object would result in a unique type of sound being generated.

Granularity proves to be a useful model for understanding complex sound phenomena. Complex waveforms can be viewed as constellations of primitive units of energy, where each unit is bounded in time and frequency space. There are numerous parallels between granular synthesis and wavelet theory.

The grain proves to be a useful representation because it combines time-domain information (envelope and waveform) with frequency-domain information (waveform period inside the grain, waveform spectrum). This is different from representations that do not capture frequency-domain information, and Fourier-derived representations that presume that sounds are summations of infinitely long sinusoids.

An amplitude envelope shapes each grain. This envelope can vary in implementation from a Gaussian curve to nonlinear functions. Complicated envelopes, like band-limited pulses, describe resonant grains that sound like woodblock taps in sparse textures when the grain duration falls below 100 ms. Narrow envelopes create popping textures when the total grain duration falls to less than 20 ms. Sharp changes in the envelope function cause strong perturbation of the spectrum. This effect is due to the convolution of the envelope's spectrum with that of the grain waveform. The grain duration can be constant, random, or it can vary in a frequency-dependent way. This implies that we should assign shorter durations to high-frequency grains. The waveform within the grain, in the case of our system, is synthetic, and is the sum of sinusoids scanned at a specified frequency.

Several parameters are varied on a grain-by-grain basis: duration, envelope, frequency, spatial location, waveform (a wave-table). This grain-by-grain level of control leads to some unique spectral effects that are only possible by using this method.

In a preferred embodiment, granular synthesis is implemented using either a simple sine wave oscillator (as described above) controlled by an envelope generator or a wave-terrain approach. In opposition to the simplicity of the sine-wave oscillator, the generation of even a simple sound requires a massive quantity of control: thousands of parameters per. These parameters describe each grain in terms of starting time, amplitude, etc. Since it is cumbersome to specify the parameters of each grain programmatically, a higher-level system of organization is required. This system should generate the grain specifications.

The complex spectrum generated by granular synthesis is proportional to the quantity of control data. If n is the number of parameters for each grain, and d is the average grain density per second of sound, it takes d * n parameter values to specify one second. Since d typically varies from a few dozen and several thousand, it is clear that for the purposes of compositional control, a higher-level unit of organization is needed. The purpose of such a unit is to allow the programmer to create instances of large quantities of grains. The synthesis method embodied by the algorithm listed we use can be classified using this granular organization model. We describe this model as an asynchronous cloud model. Clouds of a specific density are formed relative to the density of the anatomic structure or tissue being sonified. These clouds are mapped to three-dimensional space using a spatialization algorithm. Cloud microstructure is generated stochastically. Refer to FIGS. 10 and 11 for conceptual depictions of this method.

Wave Terrain Synthesis: Extracting Waveforms from Anatomy

This synthesis technique proceeds from the fundamental principle of wave-table lookup as discussed above. It is possible to extend the basic principle of wave-table lookup to the scanning of n-dimensional wave surfaces or volumes.

A traditional wave-table can be visualized in two dimensions as a function wave(x) indexed by x. A two-index wave terrain can be plotted as a function wave(x, y) on a three-dimensional surface (e.g. the surface of an anatomical object model). The z-point represents a waveform value for a given pair (x, y). The waveform is stored in a table so defined and is a function of two variables. A scan over the terrain is an orbit. Although the astronomical term "orbit" connotes an elliptical function, the orbit can consist of any sequence of points on the wave terrain.

Any three-dimensional surface can serve as a wave terrain, from a constrained function to an arbitrary projection. As in techniques like frequency modulation and wave-shaping, the advantage of using simple functions is the predictability of the derived waveform and spectrum generated by a given wave terrain function. The following conditions must be met in order to predict the derived waveform:

Both the x and y functions and their first-order partial derivatives are continuous (in the mathematical sense) over the terrain. Both functions x and y are zero on the terrain boundaries. The second property ensures that the functions and their derivatives are continuous when the orbit skips from one edge of the wave terrain to another edge. Such a skip is analogous to the right-to-left wraparound that occurs in one-index wave-table scanning. A terrain which satisfies these conditions is defined by the following equation:

$$\mathrm{wave}(x,y)=(x-y)*(x-1)*(x+1)*(y-1)*(y+1)$$

The signal generated by wave terrain synthesis depends on both the wave terrain and the trajectory of the orbit. The orbit can be a straight or curved line across the surface, a random walk, a sinusoidal function, or an elliptical function generated by sinusoidal terms in both the x and y dimensions.

When the orbit is fixed, the resulting sound is a fixed waveform characterized by a static spectrum. A way to generate time-varying (and consequently interesting, or memorable) waveforms is to change the orbit over time. Our implementation of this approach is an extension where the orbit is fixed but the wave terrain is variable over time. In this case, the wave-scanning process employs three-dimensional surfaces found in the anatomical dataset. The position of the instrument in three-dimensional space, which is used as a cursor for the surgeon, also functions as an index for the terrain scanning process. The resulting waveform is time-discretized to form grains.

The wave terrain technique provides a robust model in the context of a sonification method intended for providing feedback with respect to the navigation of a cursor through and over three-dimensional volumes and surfaces. In this approach the three-dimensional surface of any object may be interpreted as a wave terrain. Upon intersection or penetration of an object by the surgical instrument, the algorithm may orbit at a fixed or programatically defined frequency and scan path across a region of the surface, defined by a projective function perpendicular to some predetermined axis of the instrument, and the surface normal of some voxel closest to the point of contact. This is, in effect, the sonic analogue of a surface rubbing.

Three-dimensional Audio Spatialization Filterinq

While human beings are generally considered sight-dependent creatures, there is no disputing the importance of auditory cues in our ability to relate to the environment. At the physiologic level, sound waves are transmitted to the inner ear via a system of mechanical interaction between membranes, small bones, and channels containing a fluid medium. In the inner ear, the sound waves of particular frequencies are deflected in such a way as to disturb the position of hair cells that trigger neuronal connections traveling through the auditory nerve to the cerebral cortex. These impulses are interpreted by the brain as sounds of a particular pitch and intensity.

The sense of hearing includes the ability to locate sound sources in three-dimensional space: "It was Lord Rayleigh (1907) who proposed that we localized sound sources by exploiting intensity and phase differences between the signals from the left and right ears." 57 Moreover, the impact of each individual's head-shape and external ear on the reflected sound waves received by the inner ear is crucial for sound localization.

Research by Shaw (1974) demonstrated that the pinna has a significant influence on shaping the spectral envelope of incident sound. Furthermore, this spectral shaping is dependent upon the spatial origin of the sound source. Thus the brain learns to extract spatial information from the unique 'earprint' the pinnae impress upon the incoming pressure waves." Each individual therefore receives the sound waves generated by an auditory source in a slightly different way, and then, using cues based on phase and intensity differences and the information derived from the impact of one's pinnae and head on the sound waves, can localize the sound source in three dimensions, including azimuth, elevation, and distance from the listener.

More specific investigation of what factors influence sound localization has added four other parameters in addition to the factors of interaural time delay, head shadow, pinna response, and shoulder echoes that comprise the "Head-Related Transfer Function." They include head motion, vision, intensity, and early echo response and reverberation caused by local acoustics The particular interference characteristics of an individual's head-shape and pinnae on the transfer of sound waves to the ear canals is a measurable function that has generated one approach to virtual sound modeling. Various techniques involving speaker arrays and sensitive miniature microphones inserted into the ear canal make it possible to derive an individual's "Head-Related Transfer Functions (HRTFs)," which actually include the impact of the head, shoulders, and external ear on the incoming sound waves. Once the characteristics of particular sound waves that the listener localizes to a specific point is known, these sound waves can potentially be reproduced artificially, in order to give the listener the impression that the sound source is located in a specific place, whatever the location of the speakers generating the actual sound waves.

However, incorporating sound into a virtual reality application can be accomplished in a number of vastly different ways, with widely different intentions. At the most fundamental level, immersive virtual reality applications are given increased validity and realism when they make use of natural-seeming audio effects, even when such effects are not that closely tied to the visual environment, as they exploit the natural cognitive tendency of the listener to associate logically-associated sensory inputs: "Although a loudspeaker may be displaced from the actual location of a visual image on a television or movie screen, we can easily imagine the sound as coming from an actor's mouth or from a passing car. This is an example of what is termed visual capture; the location of the visual image 'captures' the location derived from audio cues." These effects can be as simple as the triggering of an unmodified pre-stored audio sound when the user acts in a particular way in the virtual environment. They need not be highly sophisticated aural effects calculated for each particular user in order to have a significant effect on the quality of the virtual environment: "A New York Times interviewer, writing on a simulation of a waterfall. . . described how 'the blurry white sheet' that was meant to simulate a waterfall through a $30,000 helmet-mounted display seemed more real and convincing with the addition of the spatialized sound of the water." 61 In this particular case, the addition of a comparatively cheap and easy to incorporate technology, generally appreciable by any user, considerably improved the overall impression of the simulation.

The vast potential of aural feedback to improve the quality of virtual reality systems is clearly at present largely underutilized, and, in the field of medical applications, virtually untested: "high-resolution color graphic hardware and software have been around longer on personal computers than the audio equivalent, CD-quality two-channel digital sound." This potential, however, should be obvious even to the observer unfamiliar with the state of virtual reality technology. Simply stated, "one might be able to work more effectively within a VR environment if actions were accompanied by appropriate sounds that seemingly emit from their proper locations, in the same way that texture mapping is used to improve the quality of shaded images." At the most basic level, therefore, pursuing the potential applications of audio technology for virtual reality is a fruitful avenue of research.

The benefits of the more sophisticated types of audio feedback in virtual reality are potentially much greater: "Although digitized sound samples play an important role in these systems, it is the ability to shape a waveform and adjust features such as pitch, timbre, amplitude, phase and decay that make it an important technology for VR. While as previously noted, digital imaging technology, volume-rendering, and visual display technology are currently stretching the limitations of currently-available computer processing speed and memory, in the case of audio technology, "current generation hardware is already capable of supplying binaural signals that model the attenuation of pressure waves entering the user's ear canals, and thus simulate the way our ears influence perceived sounds in the real world."

Sonification Algorithms

Listed below are several algorithms used in accordance with a preferred embodiment of the present invention.

Algorithm 1: Discrete Error Function

```
1   loop
2       serial_write( polhemus, request_datapoint
3       update.position = serial_read( polhemus
4       midi_plan = which_plan( midi, update.position.x
5       if( update.position.yz == midi~lan.position.yz
6           serial write( midi, midi_plan.note_on
7       else
8           serial write( midi, midi_plan.note_off )
9       endif
10      x_function.note on = which_note( update.position.x,
            midi_plan, trajectory_len.x )
11      serial write( midi, x function.note on
12      aiff_plan = which_plan( aiff, update.position.x )
13      if( update.position.yz == aiff_plan.position.yz )
14          play_aiff ( aiff_plan.aiff, aiff_plan.volume )
15      endif
16  endloop
```

FIG. 6 provides an illustration of the discrete error function in the y, z plane, using the above algorithm and the hardware system of FIG. 2.

Algorithm 2: Beat Interference

```
1   ref_frequency = a
2   loop
3       cursor = get_instrument_position()
4       plan = find nearest_point( target_path, cursor )
5       if( cursor != plan )
6           oscillator_a << ref_frequency
7           oscillator_b << ref_frequency - ( plan - cursor )
8       else
9           oscillator_a << ref_frequency
10          oscillator_b << ref_frequency
11      endif
12  endloop
```

Figure 7:
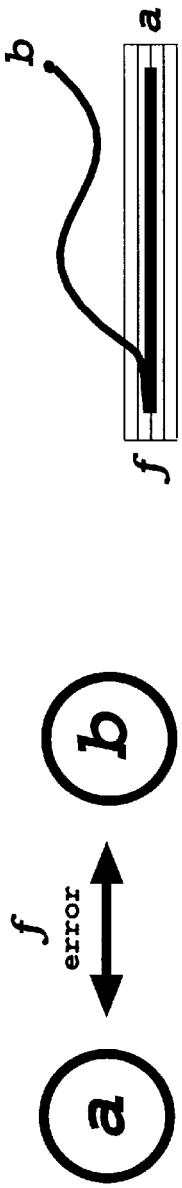
FIG. 7 illustrates an audio measurement (ruler) function used in a preferred embodiment of the present invention to assist the surgeon in determining the distance between an origin and any desired point.
Figure 7:
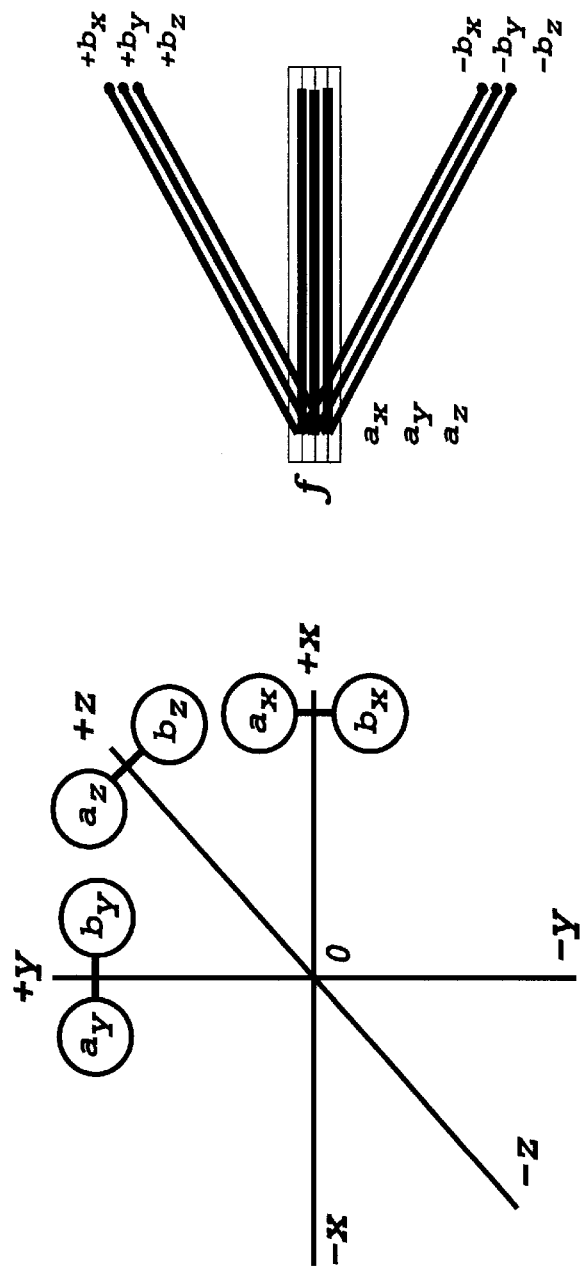

FIG. 7 provides an illustration of the beat interference error function as generated using the algorithm set forth above, and implemented upon the preferred embodiment hardware system depicted in FIG. 3. An extension of this algorithm, employing three reference frequencies and six oscillators, is also depicted.

Algorithm 3

```
1   loop
2       cursor = get_instrument_position()
3       plan = find_nearest_point( target_path, cursor )
4       spatial_location = plan - cursor
5       dsp << convolve( error_signal, spatial location )
6   endloop
```

FIG. 8 provides an illustration of the three-dimensional error function as generated using the algorithm set forth above, and implemented upon the preferred embodiment hardware system depicted in FIG. 3. This three-dimensional filtration algorithm may also be employed as a redundancy measure and extension to any of the other algorithms by providing three-dimensional spatialization of their output audio signals.

Algorithm 4

```
1   loop
2       loop
3           if( select_point() )
4               origin = get_instrument_position()
5               exit loop
6           endif
7       endloop
8       set tracking_device_origin( origin )
9       loop
10          cursor = get_instrunent position()
11          radius = cartesian_distance( cursor, origin )
12          if( 0 = modulo(radius, large_increment )
13              oscillator << large_increment_click
14          elsif( 0 = modulo( radius, small_increment )
15              oscillator << small_increment_click
16          endif
17      endloop
18  endloop
```

Figure 9:
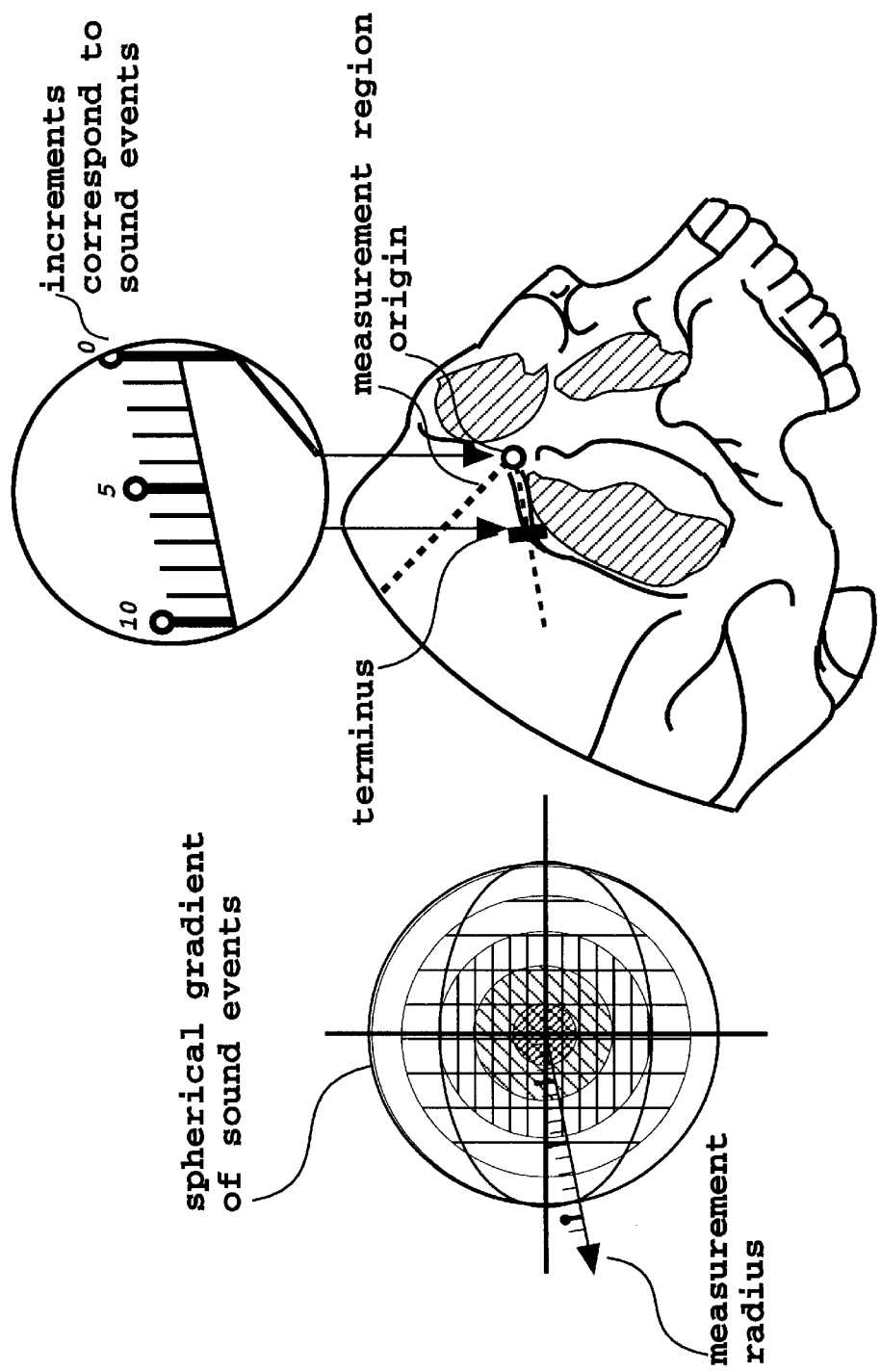
FIG. 9 provides an illustration of the line of sight audio ruler function used in a specific embodiment.

FIG. 9 provides an illustration of the line of sight audio ruler function as generated using the algorithm set forth above, and implemented upon the preferred embodiment hardware system depicted in FIG. 3.

Algorithm 5

```
    loop
2       cursor = get_instrument_position ()
3       if( intersected_object( cursor )
4           object = get_object( cursor )
5           if( random() <= object.density )
6               wave.grain_function = make_grain( object.tissue_type )
7               wave.amplitude = make_amplitude( object.density, cursor.velocity )
8               ... // Map other parameters
9               oscillator << wave
10          endif
11      endif
12  endloop
```

FIGS. 10–11 provide an illustration of the granular synthesis-based anatomical sonification function as generated using the algorithm set forth above, and implemented upon the preferred embodiment hardware system depicted in FIG. 3.

It should be understood that the foregoing description is only illustrative of the invention. Various alternatives and modifications can be devised by those skilled in the art without departing from the spirit of the invention. Accordingly, the present invention is intended to embrace all such alternatives, modifications and variances which fall within the scope of the appended claims.

We claim:

1. A computer based system for positioning an article relative to a surgical target path using audio feedback, comprising:

a memory storing a surgical target path expressed in terms of two or more spatial coordinates along a three dimensional surface representing a model of an anatomical object, the values of said spatial coordinates being indicative of a desired trajectory of said article along the surgical target path;

one or more sensors tracking the actual trajectory of the article during surgical execution;

a comparator providing on output differences between the desired trajectory and the actual trajectory of the article along said two or more spatial coordinates;

a processor translating the provided differences along said two or more spatial coordinates into corresponding two or more coordinates of an audio space; and audio means for playback of said two or more coordinates of the audio space to assist in positioning the article relative to the surgical target path.

2. The system of claim 1 wherein said processor translates the provided differences into sound grains of predetermined duration.

3. The system of claim 2 wherein the duration of the sound grains is between 1 and 100 ms.

4. The system of claim 2 wherein parameters characterizing the sound grain are in the group comprising: duration, envelope and frequency.

5. The system of claim 1 wherein the processor translates the provided differences based on user-specific input.

6. The system of claim 1 wherein the memory stores two or more surgical target paths associated with a patient.

7. The system of claim 1 wherein the memory stores two or more surgical target paths associated with different patients.

8. The system of claim 1 wherein at least one of said two or more coordinates of the audio space corresponds to a recognizable audio theme.

9. The system of claim 1 wherein the processor comprises means for automatically selecting different coordinates of the audio space based upon the surgical target path and the actual trajectory of the article during surgical execution.

10. The system of claim 1 further comprising visual means for advising the surgeon.

11. The system of claim 1 further comprising correction means for changing the surgical target path during surgery and determining a new surgical target path based, at least in part, upon previously sensed surgical execution.

12. The system of claim 11 wherein the correction means comprises a voice responsive input means.

13. The system of claim 1 further comprising means for advising the surgeon, said means for advising including means for automatically providing a resistance force to motion of the article in at least one degree-of-freedom.

14. The system of claim 1 wherein the article is a surgical instrument.

* * * * *